(12) United States Patent
Tornier

(10) Patent No.: US 6,890,357 B2
(45) Date of Patent: May 10, 2005

(54) ELBOW PROSTHESIS

(75) Inventor: Alain Tornier, Saint Ismier (FR)

(73) Assignee: Tornier, Saint-Ismier (FR)

( * ) Notice: Subject to any disclaimer, the term of this patent is extended or adjusted under 35 U.S.C. 154(b) by 0 days.

(21) Appl. No.: 10/849,899

(22) Filed: May 21, 2004

(65) Prior Publication Data

US 2004/0243243 A1 Dec. 2, 2004

Related U.S. Application Data

(60) Provisional application No. 60/473,446, filed on May 28, 2003.

(30) Foreign Application Priority Data

May 28, 2003 (FR) .............................................. 03 06519

(51) Int. Cl.$^7$ .................................................. A61F 2/38
(52) U.S. Cl. .................................................. 623/20.12
(58) Field of Search .......................... 623/20.11, 20.12, 623/20.13

(56) References Cited

U.S. PATENT DOCUMENTS 4,383,337 A    5/1983  Volz et al.
6,379,387 B1 * 4/2002  Tornier ..................... 623/20.12
6,767,368 B2 * 7/2004  Tornier ..................... 623/20.12
2002/0165614 A1  11/2002  Tornier
2003/0208277 A1  11/2003  Weiss et al.

FOREIGN PATENT DOCUMENTS

EP      0913133      5/1999
EP      1051954      11/2000

* cited by examiner

Primary Examiner—Eduardo C. Robert
(74) Attorney, Agent, or Firm—Dowell & Dowell, P.C.

(57) ABSTRACT

A humeral component, forming a first articulating surface, and an ulnar component forming a second articulating surface adapted to be disposed around a part of the first articulating surface and to pivot about its longitudinal axis. This ulnar component is provided with structure for mounting a locking element which forms a third articulating surface extending the second and adapted likewise to be disposed around a part of the first surface. These mounting structure comprise guiding structures adapted to cooperate with complementary structure provided on the locking element in order to guide this element in translation with respect to the ulnar component, up to a position where blocking structure provided respectively on the locking element and on the ulnar component may be employed to immobilize this element on this component, these blocking structure being able to be employed only in this position.

10 Claims, 4 Drawing Sheets

ELBOW PROSTHESIS

This application claims the benefit of U.S. provisional application No. 60/473,446 filed May 28, 2003.

FIELD OF THE INVENTION

The present invention relates to an elbow prosthesis comprising at least one humeral component and one ulnar component.

It concerns more particularly an elbow prosthesis of which the ulnar component is adapted to receive a locking element which forms an articulating surface extending that of the ulnar component, the articulating surfaces of the locking element and of the ulnar component being adapted to be arranged together around at least a part of another articulating surface belonging to a humeral component. A prosthesis of this type is known from EP-A-1 051 954.

BACKGROUND OF THE INVENTION

In such a prosthesis, the locking element is maintained in position on the ulnar component thanks to a screw introduced in a through housing in this element and tightened in a tapping provided on the ulnar component. It has proved in practice that the positioning of the locking element on the ulnar component is not always optimum when such a screw is tightened, which may lead to a skewed positioning of the screw with respect to the tapping, to such a point that the thread of the screw or the tapping may be distorted, thus preventing the locking element from being mounted. In addition, the afore-mentioned screw serves both to bring the locking element into correct position with respect to the ulnar component and to ensure blocking of these two elements with respect to each other. As a result, such an ulnar component must most often be fitted while the articulation of the elbow is in maximum flexion, which renders the surgeon's work more complex. It even happens that such fitting in maximum flexion is not possible, particularly in the case of marked obesity of the patient.

It is a more particular object of the invention to overcome these drawbacks by proposing an elbow prosthesis whose fit is facilitated, when it comprises a locking element as mentioned hereinabove.

SUMMARY OF THE INVENTION

To that end, the present invention relates to an elbow prosthesis comprising a humeral component, forming a first articulating surface, and an ulnar component forming a second articulating face adapted to be disposed around a part of the first articulating surface and to pivot about a longitudinal axis of this surface, the ulnar component being provided with means for mounting a locking element which forms a third articulating surface extending the second articulating surface and adapted likewise to be disposed around a part of the first articulating surface. This prosthesis is characterized in that the afore-mentioned mounting means comprise guiding means adapted to cooperate with complementary means provided on the locking element in order to guide this element in translation with respect to the ulnar component, up to a position where blocking means provided respectively on the locking element and on the ulnar component may be employed to immobilize the locking element on the ulnar component, these blocking means being able to be employed only in this position.

Thanks to the invention, the guiding means ensure an adequate positioning of the locking element with respect to the ulnar component before the blocking means are employed to effect an efficient immobilization of the locking element with respect to the ulnar component. In other words, the blocking means do not serve to bring the locking element in a configuration allowing its blocking, this function being performed by the guiding means which may be positioned and configured to ensure this function best.

In addition, an elbow prosthesis may incorporate one or more of the following characteristics, taken in any technically admissible combination:

The blocking means comprise a screw and a complementary tapping provided respectively on the locking element and on the ulnar component, or vice versa, the direction of relative translation between the locking element and the ulnar component as imposed by the guiding means being non-parallel to the longitudinal axis of the tapping and/or of the afore-mentioned screw.

The guiding means comprise at least one element in relief projecting with respect to a principal part of the ulnar component, while the complementary means provided on the locking element are adapted to interact with this element in relief by cooperation of shapes. In that case, the afore-mentioned element in relief may be a nose, while the complementary means comprise a fork of which two branches define therebetween a volume for receiving and for slide of this nose.

The guiding means and the blocking means are arranged in the vicinity of two opposite edges of the second articulating surface of the ulnar component, while the complementary means and the blocking means provided on the locking element are arranged on two opposite edges of that element.

The blocking means comprise a screw and a tapping, which are complementary and respectively provided on the locking element and on the ulnar component, or vice versa, while means are provided for blocking this screw in rotation. The head of the screw may thus be of non-circular section, while the piece against which this head bears forms a space for receiving this head, with contact between the surface of this piece and the outer surface of the head. More particularly, the head of the screw may be provided with catch elements adapted to penetrate superficially in the surface of the afore-mentioned piece. In a variant, the piece against which the head of the screw bears may be provided with a tab foldable into configuration of blockage of this head. In that case, the head of the screw may be of polygonal profile, with faces whose width is greater than the width of the foldable tab.

BRIEF DESCRIPTION OF THE DRAWINGS

The invention will be more readily understood and other advantages thereof will appear more clearly in the light of the following description of a form of embodiment of a prosthesis in accordance with its principle, given solely by way of example and made with reference to the accompanying drawings, in which.

DESCRIPTION OF PREFERRED EMBODIMENT

Figure 1:
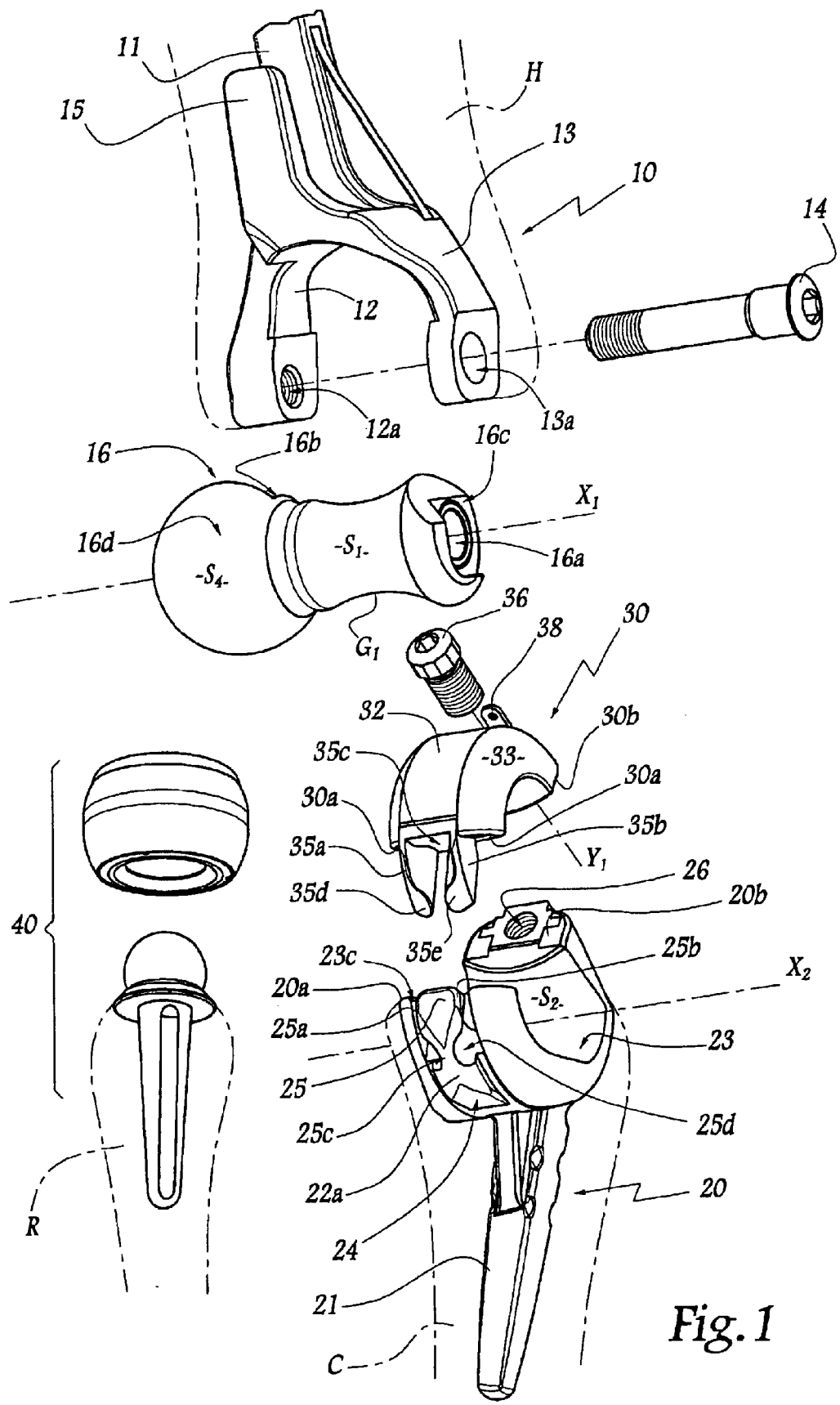
FIG. 1 is an exploded view in perspective of an elbow prosthesis according to the invention.
Figures 2, 3:
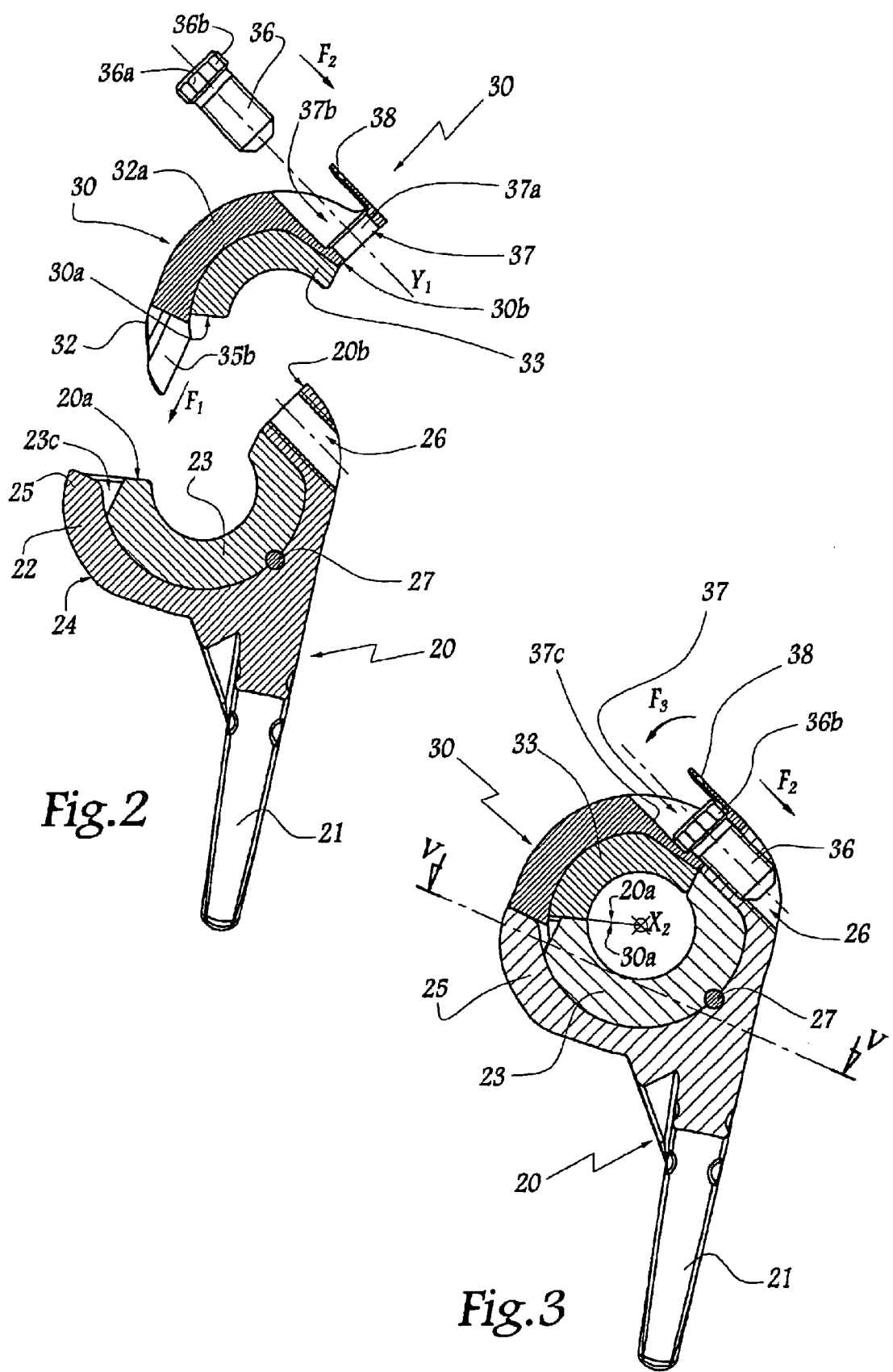
FIG. 2 is a longitudinal section of the ulnar component and of the locking element in the course of assembly.
FIG. 3 is a section similar to FIG. 2 while the locking element is mounted on the ulnar component.
Figure 4:
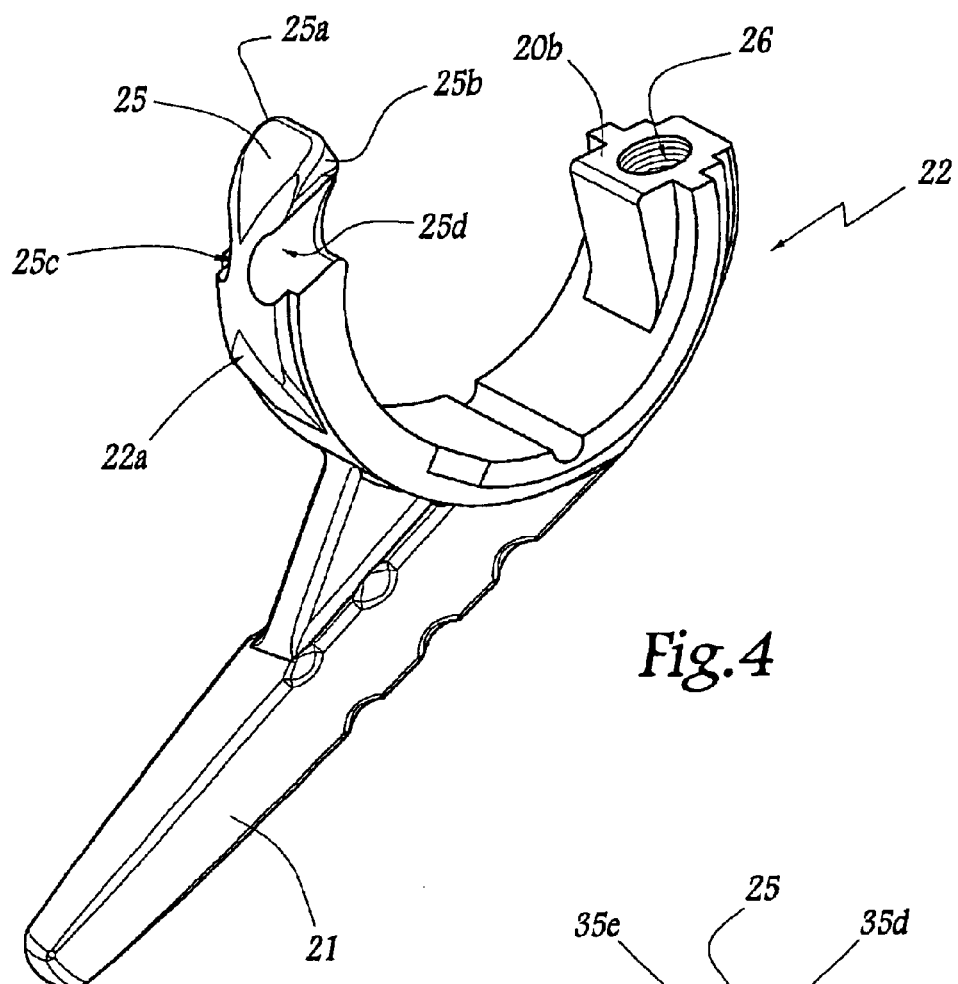
FIG. 4 is a view in perspective of the metal part of the ulnar component.
Figure 5:
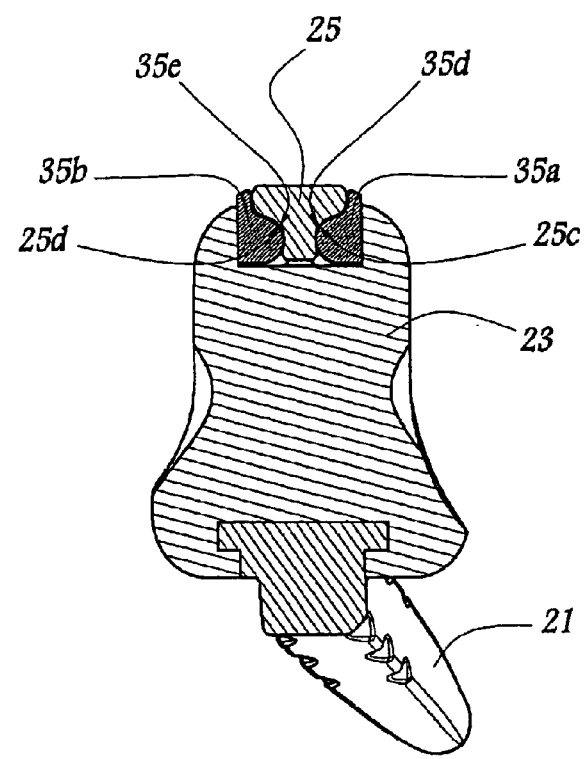
FIG. 5 is a section along line V—V of FIG. 3.
Figure 6:
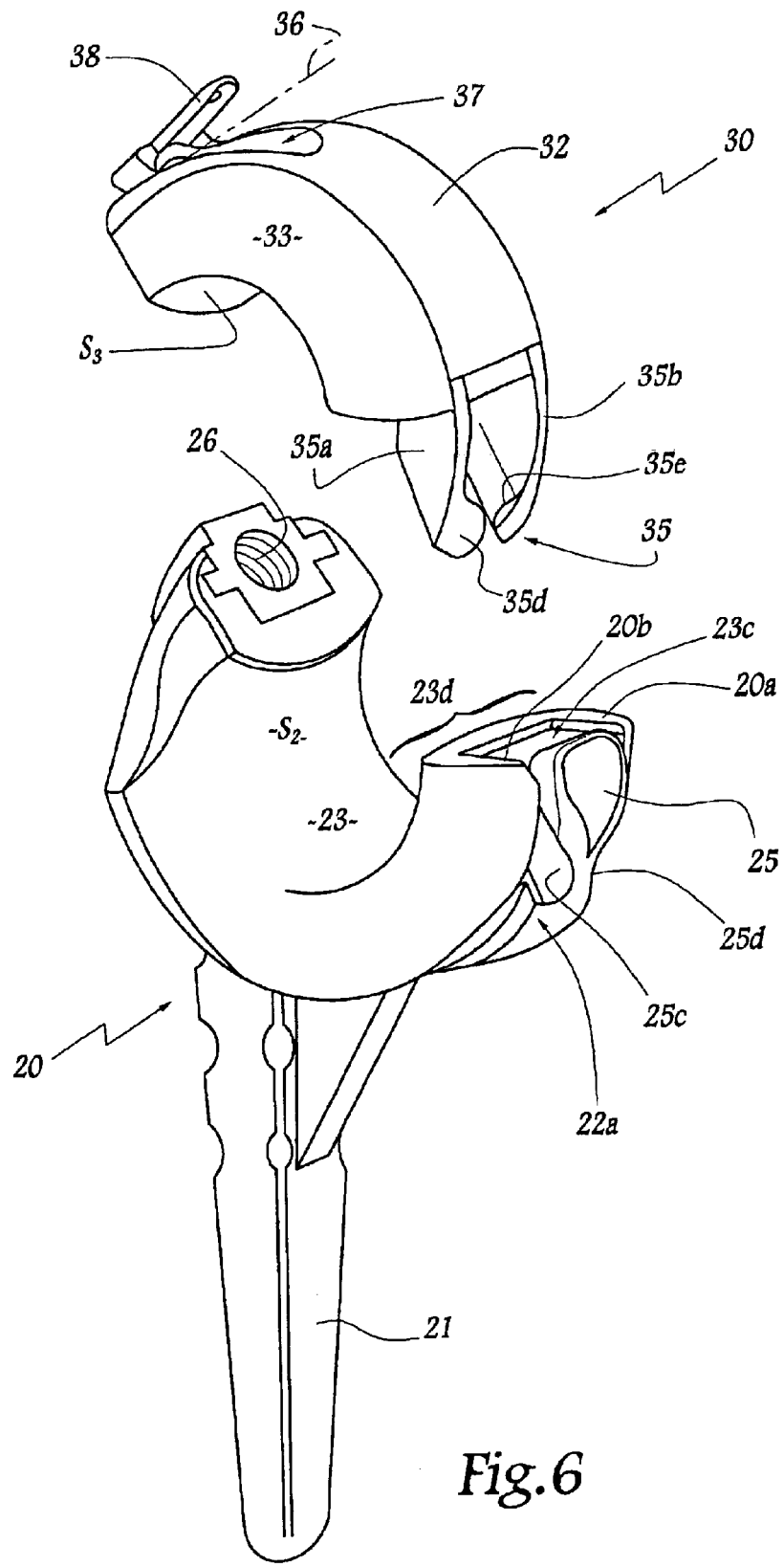
FIG. 6 is a view in perspective of the ulnar component and of the locking element of the prosthesis, on a larger scale.

Referring now to the drawings, the prosthesis visible in FIGS. 1 to 3 comprises a humeral component 10 comprising a stem 11 intended to be driven in the medullary canal of a humerus H and extending in two branches 12 and 13, each pierced with an orifice 12a, 13a for passage of a hollow screw 14 forming pin. The hollow nature of the screw 14 allows the passage of suture yarns. The orifice 12a is tapped, allowing the screw 14 to be screwed. The stem 11 also extends in a third branch 15 intended to come into abutment against the cortex of the humerus.

An elongated piece 16 is provided with a central bore 16a whose dimensions are such as to receive the screw 14, this making it possible to mount the piece 16 between the branches 12 and 13. The piece 16 is provided with two end surfaces 16b and 16c provided to come respectively into contact with the opposite surfaces of the branches 12 and 13.

Between the surfaces 16b and 16c, the piece 16 is substantially cylindrical, with circular base, and forms a surface of articulation $S_1$ which is also substantially cylindrical, whose generatrix $G_1$ is curved and concave, in that the diameter of the surface $S_1$ is minimum in the central part of the piece 16 included between the surfaces 16b and 16c. $X_1$ denotes the axis of symmetry of the surface $S_1$.

The piece 16 extends in an extension 16d whose outer surface $S_4$ is convex and which covers the branch 12 when the piece 16 is mounted between the branches 12 and 13.

The whole of the humeral component 10 is made of metal.

The ulnar component 20 comprises a metal stem 21 intended to be inserted in the medullary canal of the ulna C and which is in one piece with a branch 22 likewise made of metal, of concave shape and whose inner surface is covered with a lining 23 made of a material adapted to the friction with the metal piece 16, for example polyethylene. The lining 23 is mounted on the branch 22 by cooperation of shapes. A pin 27 makes it possible to immobilize elements 22 and 23 with respect to each other.

The inner surface of the lining 23 forms a surface of articulation $S_2$ whose shape is complementary to that of surface $S_1$. $X_2$ denotes the central axis of elements 22 and 23.

The respective diameters of surfaces $S_1$ and $S_2$, which diameters are variable along axes $X_1$ and $X_2$, are chosen so that the surface $S_2$ may be disposed around the surface $S_1$, with a slight clearance, this allowing a rotation of the components 10 and 20 with respect to each other about axes $X_1$ and $X_2$ which, in that case, merge.

Moreover, the profiles of the generatrices of surfaces $S_1$ and $S_2$ are chosen so as to allow a degree of mobility of the surface $S_1$ in surface $S_2$, in the sense of varus-valgus, i.e. about an axis perpendicular to $X_1$ and $X_2$.

A locking element 30 is intended to be mounted on the component 20 and comprises a metal casing 32 and a lining 33 immobilized with respect to each other by clipping. The lining 33 is advantageously made of the same material as the lining 23 and forms a concave articulating surface $S_3$ intended to extend the surface $S_2$ and, with it, surround the surface $S_1$.

In order to facilitate assembly of the element 30 on the component 20, this component is provided, in extension of the outer surface 24 of the branch 22, with an element in relief 25 in the form of a nose or beak which projects beyond the part 22a of the branch 22 covered by the lining 23.

Furthermore, the casing 32 of the element 30 extends beyond its part 32a covered by the lining 33, in an extension in the form of a fork 35 of which the two branches 35a and 35b together define a volume 35c for slide and reception of the nose 25 when the element 30 is mounted on the component 20.

The nose 25 is disposed in a space 23c defined by the lining 23 which extends beyond the part 22a of the branch 22 that it covers. In its part 23d which extends in overhang with respect to the part 22a, the lining has a substantially U-shaped cross-section. The space 23c is defined at the centre of this U.

The nose 25 has a width decreasing in the direction of the bottom of the U formed by the part 23d. In this way, the sides 25a and 25b of the nose 25 diverge, moving away from this bottom and approaching the branches of the U formed by the part 23d. The nose 25 has a section substantially in the form of a dove-tail.

In addition, grooves 25c and 25d are formed on either side of the nose 25. These grooves have profiles allowing them to receive convex parts 35d and 35e of the branches 35a and 35b.

The branches 35a and 35b thus have a geometry compatible with their introduction in the space 23c, on either side of the nose 25. Their surfaces intended to face towards the nose 25 deviate from each other towards the outside of the element 30, with the result that these surfaces are substantially parallel to sides 25a and 25b.

In this way, the direction of assembly of the element 30 on the component 20 is necessarily that indicated by arrow $F_1$ in FIG. 2, this direction being imposed by the cooperation of shapes between the nose 25 and the fork 35. In effect, as indicated hereinabove, the transverse sections of the nose 25 on the one hand and of the inner parts of the branches 35 are chosen to impose this direction of slide.

Furthermore, the component 20 is provided with a tapping 26 for receiving a screw 36 which traverses a through housing 37 provided to that end in the element 30.

The tapping 26 and the housing 37 are configured so that they are aligned, in a direction $Y_1$ perpendicular to axis $X_2$, at the end of the slide of the element 30 with respect to the component 20. Such slide takes place until the linings 23 and 33 come into abutment against each other in the vicinity of the members 25 and 35, as shown in FIG. 3. It is then possible to screw the screw 36 in the tapping 26, in the direction of arrow $F_2$ in FIGS. 2 and 3. In the configuration of FIG. 3, the central axes of the screw 36 and of the tapping 26 merge and are parallel to direction $Y_1$.

The direction $Y_1$ is not parallel to the direction of displacement of the element 30 with respect to the component 20 during its assembly, i.e. to arrow $F_1$, with the result that the screw 36 can be introduced in the tapping 26 only at the end of slide of the element 30 on the component 20 in the direction of arrow $F_1$.

In this way, the screw 36 serves solely for blocking the element 30 in position on the component 20 and can be tightened only once a correct position of the element 30 on the component 20 has been attained. The risks of the screw 36 being tightened askew in the tapping 26 are thus avoided.

In addition, the mechanical strength of the assembly formed by the elements 20 and 30 in the configuration of FIG. 3 is much greater than that able to be obtained with the prosthesis known from EP-A-1 051 954 as, once the screw 36 is tightened, the element 30 is immobilized with respect to the component 20 on its two sides.

In effect, the nose 25 is provided in the vicinity of a first edge 20a of the component 20 and of the surface $S_2$, while the tapping 26 is provided near the opposite edge 20b of this component. In the same way, elements 35 and 37 are respectively provided in the vicinity of the two opposite edges 30a and 30b of the element 30 and of the surface $S_3$.

In other words, the function of guiding of the element 30 with respect to the component 20 is obtained in the vicinity of the edges 20a and 30a of these members, while the function of blocking is obtained in the vicinity of the edges 20b and 30b.

The housing 37 is formed by a circular orifice 37a made in the metal casing 32 for the passage of the shank of the screw 36, as well as by a concave zone 37b made in an end part of the lining 33, in the vicinity of the edge 30b.

The head 36a of the screw 36 presents a non-circular external section as it is equipped with peripheral catching elements or teeth 36b provided to engage superficially in the inner radial surface 37c of the concave zone 37b, this contributing to the immobilization of the screw 36 in rotation and thus ensures an efficient blocking of the element 30 on the component 20.

In addition, a tab 38 extends the casing 32 in the vicinity of the housing 37, this tab being able to be folded into abutment against the head 36a of the screw 36 when the latter is tightened, in the direction of arrow $F_3$ in FIG. 3, so that it performs a function of non-return for this screw, this also contributing to the efficient blocking of the element 30 on the component 20.

According to a variant embodiment of the invention (not shown), the head 36a may present a polygonal profile, for example hexagonal or octagonal, with planar faces. In that case, the width of the tab 38 is chosen to be less than the width of the lateral faces of this head, this allowing the screw 36 to be blocked in rotation by surface abutment of one of these faces against this tab.

When the element 30 is mounted on the component 20, the assembly thus produced may pivot about axis $X_1$ and the joining of surfaces $S_2$ and $S_3$ surrounds the surface $S_1$ over 360°.

A radial component adapted to be mounted on the radius R is advantageously provided in the prosthesis according to the invention, this component 40 defining a surface intended to cooperate with the surface $S_4$. However, this is not compulsory.

The invention is not limited to the sole form of embodiment represented. In particular, it may concern a prosthesis in which the projecting element, such as the nose 25, is provided on the element 30, while a structure of fork type is provided on the ulnar component. Similarly, the tapping for receiving the blocking screw may be provided on the locking element, the ulnar component in that case defining a housing for receiving the locking screw.

Any mechanical means for blocking the locking element on the ulnar component may be envisaged within the framework of the present invention.

What is claimed is:

1. Elbow prosthesis comprising a humeral component, forming a first articulating surface, and an ulnar component forming a second articulating surface adapted to be disposed around a part of said first articulating surface and to pivot about a longitudinal axis of said first articulating surface, said ulnar component being provided with means for mounting a locking element which forms a third articulating surface extending said second articulating surface and adapted likewise to be disposed around a part of said first articulating surface, wherein said mounting means comprise guiding means adapted to cooperate with complementary means provided on said locking element in order to guide said element in translation with respect to said ulnar component, up to a position where blocking means provided respectively on said locking element and on said ulnar component may be employed to immobilize said locking element on said ulnar component, said blocking means being able to be employed only in this position.

2. The prosthesis of claim 1, wherein said blocking means comprise a screw and a complementary tapping provided respectively on said locking element and on said ulnar component, or vice versa, the direction of relative translation between said element and said component as imposed by said guiding means being non-parallel to the longitudinal axis of said tapping and/or of said screw.

3. The prosthesis of claim 1, wherein said guiding means comprise at least one element in relief projecting with respect to a principal part of said ulnar component, while the complementary means provided on said locking element are adapted to interact with said element in relief by cooperation of shapes.

4. The prosthesis of claim 3, wherein said element in relief is a nose, while said complementary means comprise a fork of which two branches define therebetween a volume for receiving and for slide of said nose.

5. The prosthesis of claim 1, wherein said guiding means and said blocking means are arranged in the vicinity of two opposite edges of said second articulating surface, while said complementary means and the blocking means provided on said locking element are arranged on two opposite edges of said locking element.

6. The prosthesis of claim 1, wherein said blocking means comprise a screw and a tapping, which are complementary and respectively provided on said locking element and on said ulnar component, or vice versa, and means are provided for blocking said screw in rotation.

7. The prosthesis of claim 6, wherein the piece against which the head of said screw bears, is provided with a tab foldable into configuration of blocking of said head.

8. The prosthesis of claim 7, wherein the head of said screw is of polygonal profile, with faces whose width is greater than the width of said foldable tab.

9. The prosthesis of claim 6, wherein the head of said screw is of non-circular section, while the piece against which said head bears, forms a space for receiving said head, with contact between the surface of said piece and the outer surface of said head.

10. The prosthesis of claim 9, wherein said head is provided with catch elements adapted to penetrate superficially in the surface of said piece.

* * * * *

UNITED STATES PATENT AND TRADEMARK OFFICE
Certificate

Patent No. 6,890,357 B2                                                            Patented: May 10, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Alain Tornier, Saint Ismier (FR); Shawn O'Driscoll, Rochester, MN (US); Graham King, London, Ontario (CA); Ken Yamaguchi, St. Louis, MO (US); Yves Alain Ratron, Grenoble (FR); and Bruno Scialom, Gieres (FR).

Signed and Sealed this Seventeenth Day of July 2012.

Eduardo C. Robert
Supervisory Patent Examiner
Art Unit 3733
Technology Center 3700